(12) United States Patent
Overes et al.

(10) Patent No.: US 9,907,591 B2
(45) Date of Patent: Mar. 6, 2018

(54) STRAND FOR MINIMALLY INVASIVE REMOVAL OF T-ANCHOR

(75) Inventors: Tom Overes, Oberdorf (CH); Bruno Walter, Solothurn (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1458 days.

(21) Appl. No.: 13/419,908

(22) Filed: Mar. 14, 2012

(65) Prior Publication Data

US 2013/0072989 A1    Mar. 21, 2013

Related U.S. Application Data

(60) Provisional application No. 61/500,306, filed on Jun. 23, 2011, provisional application No. 61/583,858, filed on Jan. 6, 2012.

(51) Int. Cl.
*A61B 17/04* (2006.01)
*A61B 17/84* (2006.01)
*A61B 90/92* (2016.01)

(52) U.S. Cl.
CPC ........ *A61B 17/842* (2013.01); *A61B 17/0401* (2013.01); *A61B 90/92* (2016.02); *A61B 2017/0417* (2013.01); *A61B 2017/0445* (2013.01)

(58) Field of Classification Search
CPC ......... A61B 17/0401; A61B 2017/0414; A61F 2/0811
USPC ............... 606/232–233, 300–331; 623/13.14
See application file for complete search history.

(56) References Cited

U.S. PATENT DOCUMENTS

| | | |
|---|---|---|
| 5,464,426 A | 11/1995 | Bonutti |
| 5,522,846 A | 6/1996 | Bonutti |
| 5,527,343 A | 6/1996 | Bonutti |
| 2005/0261710 A1* | 11/2005 | Sakamoto et al. ............ 606/139 |
| 2009/0082805 A1* | 3/2009 | Kaiser et al. ................. 606/228 |
| 2010/0114163 A1 | 5/2010 | Martin |
| 2012/0296345 A1* | 11/2012 | Wack et al. ................... 606/139 |

* cited by examiner

*Primary Examiner* — Tatiana Nobrega
*Assistant Examiner* — Jessica Weiss
(74) *Attorney, Agent, or Firm* — Fay Kaplun & Marcin, LLP

(57) ABSTRACT

An anchoring device includes (a) a flexible member extending from a proximal end to a distal end and (b) an elongated anchor member extending from a first end to a second end and attached to the distal end of the flexible member such that the anchor member is movable between an insertion configuration in which the anchor member is substantially parallel to the flexible member and a locked configuration in which the anchor member is substantially perpendicular to the flexible member in combination with (c) a flexible removal element extending from a proximal end to a distal end attached to the first end of the anchor member.

7 Claims, 5 Drawing Sheets

US 9,907,591 B2

STRAND FOR MINIMALLY INVASIVE REMOVAL OF T-ANCHOR

PRIORITY CLAIM

The present application claims priority to U.S. Provisional Application Ser. No. 61/500,306 filed on Jun. 23, 2011 and entitled "Removal Strand for T-Anchor for Minimal Invasive Removal" and U.S. Provisional Application Ser. No. 61/583,858 filed on Jan. 6, 2012 and entitled "Strand for Minimally Invasive Removal of T-Anchor," the entire disclosures of which are incorporated herein by reference.

FIELD OF THE INVENTION

The present invention relates to a device for treating a bone and, in particular, relates to an anchoring device for a bone.

BACKGROUND

T-anchors are often used in sports medicine and for fixation of the spine. For example, T-anchors may be used to treat the annulus after removal of a herniated nucleus portion of an intervertebral disc. T-anchors may also be used to provide treatment for syndesmotic injuries along with acromioclavicular (AC) and coracoclavicular (CC) joint repairs. Current T-anchors include a suture attached to a center of a bar (i.e., the anchor) such that the bar may be moved between an insertion configuration and a locked configuration. In the insertion configuration, the bar is generally held substantially parallel to the suture such that the bar and a portion of the suture may be easily inserted through a hole in the bone. Once the T-anchor has been passed through the hole in the bone to a desired position, the T-anchor is moved to the locked configuration in which the bar extends substantially perpendicular to the suture and the hole to prevent the bar from passing through the opening of the hole through which it has passed. Tension is then applied to the suture to fix the bar to the bone. These T-anchors are simple to place but are difficult to remove once they have been implanted. In most cases, an extra incision is necessary to retrieve the bar from the far side of the bone.

SUMMARY OF THE INVENTION

The present invention is directed to an anchoring device comprising a flexible member extending from a proximal end to a distal end and an elongated anchor member extending from a first end to a second end and attached to the distal end of the flexible member such that the anchor member is movable between an insertion configuration in which the anchor member is substantially parallel to the flexible member and a locked configuration in which the anchor member is substantially perpendicular to the flexible member in combination with a flexible removal element extending from a proximal end to a distal end attached to the first end of the anchor member.

DETAILED DESCRIPTION

Figure 1:
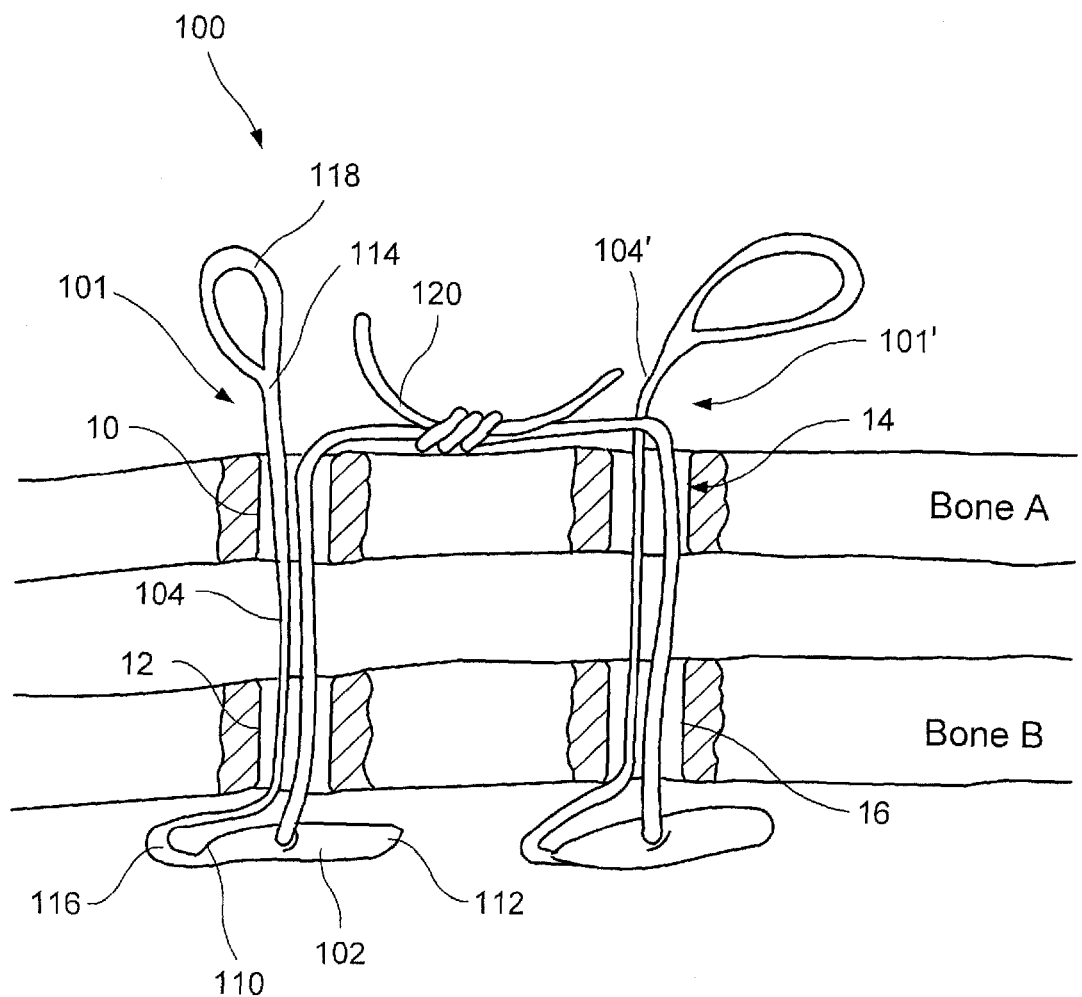
FIG. 1 shows a side view of a system according to an exemplary embodiment of the present invention.

The present invention may be further understood with reference to the following description and the appended drawings, wherein like elements are referred to with the same reference numerals. The present invention relates to a device for treating a bone and, in particular, relates to an anchoring device for a bone. Exemplary embodiments of the present invention describe a bone anchor including a removal element such that the bone anchor may be easily removed via a minimally invasive procedure subsequent to implantation thereof. Although exemplary embodiments of the present invention specifically show and describe the use of two bone anchors and the fixation of two bones relative to one another, it will be understood by those of skill in the art that any number of bone anchors may be used for the fixation of a variety of different bones, joints and soft tissue. It should be noted that the terms "proximal" and "distal," as used herein, are intended to refer to a direction toward (proximal) and away from (distal) a user of the device.

As shown in FIGS. 1-6, a system 100 according to an exemplary embodiment of the present invention comprises a bone anchor 101 including an elongated anchor member 102 attached to a distal end 106 of a flexible member 104 along with a removal element 108. The flexible member 104 is coupled, for example, to a center of the anchor member 102 such that the anchor member 102 is movable between a insertion configuration and a locked configuration relative to the flexible member 104. In the insertion configuration, the anchor member 102 extends substantially parallel to the flexible member 104 to facilitate insertion of the anchor member 102 and a portion of the flexible member 104 through corresponding holes 10, 12 in adjacent bones A, B. As would be understood by those skilled in the art, the holes 10, 12 may be drilled through the bones A, B in alignment with one another such that the bone anchor 101 may be inserted therethrough to fix the bones A, B relative to one another. Once the anchor member 102 has been inserted through the holes 10, 12, the anchor device 100 is moved to the locked configuration in which the anchor member 102 is substantially perpendicular to the flexible member 104 to prevent the anchor member 102 from passing back through the holes 10, 12, locking the anchor member 102 the bones A, B. Tension is then applied to the flexible member 104 and the flexible member 104 is then tied to a flexible member 104' of a second bone anchor 101' inserted through a second set of holes 14, 16 in bones A, B in a similar manner to fix the bones A, B relative to one another. The removal element 108 is attached to an end of the anchor member 102 such that when it is desired to remove the bone anchor 101 from the bones A, B, a surgeon or other user simply cuts the tensioned flexible member 104 while holding the removal element 108 such that the anchor member 102 falls and is substantially aligned with a length of the removal element 108 permitting the removal element 108 to be pulled proximally, drawing the bone anchor 101 through the holes 10, 12 and out of the bones A, B.

As shown in FIG. 1, the system 100 may be used to fix portions of two adjacent bones A, B relative to one another. It will be understood by those of skill in the art, however, that the system 100 may also similarly be used to fix any portion of bone or soft tissue to any other portion of bone or soft tissue. For example, the bone anchor 101 may be used for repair of the AC and CC joints, and in syndesmotic applications. It will also be understood by those of skill in the art that the system 100 may be used to fix a bone plate or other bone fixation device to a bone. Although the exemplary embodiment specifically shows the system 100 including a second bone anchor 101', which may be substantially similar to the bone anchor 101, it will be understood by those of skill in the art that a single bone anchor 101 may also be utilized. For example, the flexible member 104 may be tied or sutured to a soft tissue to fix the bone anchor 101. It will also be understood by those of skill in the art that the system 100 may include more than two bone anchors 101.

The flexible member 104 may be any flexible element such as, for example, a suture, thread, cable or wire, extending from a proximal end 120 to the distal end 106. The anchor member 102 extends from a first end 110 to a second end 112 such that the distal end 106 of the flexible member 104 is coupled to a portion of the anchor member 102 approximately midway between the first and second ends 110, 112. The anchor member 102 may be formed of any suitably strong biocompatible material as would be understood by those skilled in the art. For example, the anchor member 102 may be formed of PEEK, stainless steel, titanium alloys, nylon and/or polyethylene. In the insertion configuration, the anchor member 102 is moved relative to the flexible member 104 such that one of the first and second ends 110, 112 is positioned proximally while the other of the first and second ends 110, 112 is positioned distally permitting the anchor member 102 and a distal portion of the flexible member 104 to be easily inserted through holes 10, 12. In the locked configuration, the anchor member 102 has been moved relative to the flexible member 104 such that the anchor member 102 is substantially perpendicular to the flexible member 104 and a hole through which it is passed preventing the anchor member 102 from passing through the holes 10, 12 (e.g., a length of the anchor member 102 is greater than a diameter of the holes 10, 12), thereby locking the bone anchor 101 relative to the bones A, B.

The removal element 108 extends from a proximal end 114 to a distal end 116, which is attached to the first end 110 of the anchor member 102 such that when the bone anchor 101 is inserted through holes 10, 12 of the bones A, B, a distal portion thereof is similarly inserted through the holes 10, 12 while the proximal end 114 extends proximally from a proximal surface of the near bone (bone A). The removal element 108 may, for example, be integrally formed with the anchor member 102 (e.g., formed of a plastic material) or may be crimped together (e.g., formed of a steel material). The removal element 108 is also formed of a flexible material such that the removal element 108 flexes, as required, as the bone anchor 101 is inserted into the holes 10, 12 and moved between the insertion and locked configurations, as described above. The removal element 108 may be formed of any suitably strong, flexible, biocompatible material such as, for example, suture, thread, cable or wire.

For removal, the flexible member 104 (e.g., a flexible member 104 which has been tied to the flexible member 104' or to a soft tissue) is severed and the removal element is tensioned to move the bone anchor 101 to a removal configuration. In the removal configuration, the first end 110 remains attached to the distal end 116 of the removal element 108 while the second end 112 is loose permitting the anchor member 102 to become substantially aligned with a length of the removal element 108 as it is tensioned. Thus, the removal element 108 may be drawn proximally to remove the bone anchor 101 from the bones A, B via the holes 10, 12 through which the bone anchor 101 was initially inserted, eliminating the need for any additional incisions. The proximal end 114 may include a loop 118 which may be hooked and/or held by the user when it is desired to remove the bone anchor 101. In particular, the loop 118 may be hooked via an instrument such that the removal element 108 may be held as the flexible member 104 is cut or severed. The loop 118 may be formed of any of a variety of materials so long as the loop 118 is prevented from falling through the holes 10, 12 after insertion of the bone anchor 101 therethrough. In a preferred embodiment, the loop 118 may be formed of a soft material such as those used for surgical sutures, to prevent soft tissue irritation. In one exemplary embodiment, the removal element 108 may be colored such that the removal element 108 may be easily identified and differentiated from the flexible member 104.

Figure 2:
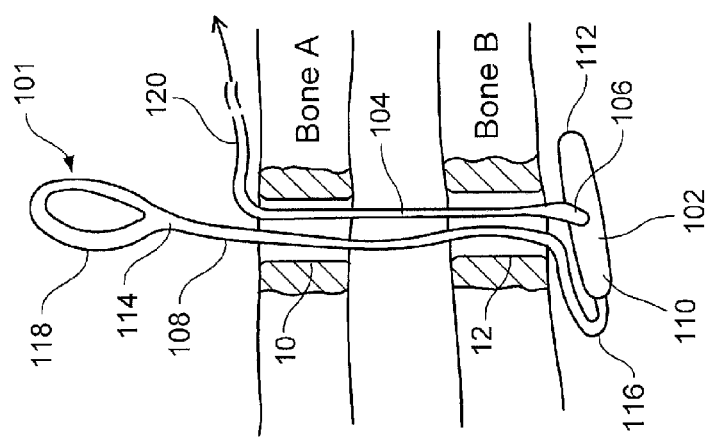
FIG. 2 shows a side view of a first anchor device of the system of FIG. 1, in a locked configuration.

According to an exemplary technique using the system 100, the first bone anchor 101 is inserted through the drilled holes 10, 12 in the bones A, B, respectively, in the insertion configuration. The bone anchor 101 is inserted through the holes such that the anchor member 102 and a distal portion of the flexible member 104 and the removal element 108 are passed through the holes 10, 12 and proximal ends 120, 114 thereof extend proximally from a proximal surface of the near bone (bone A). Once inserted, as shown in FIG. 2, the bone anchor 101 is moved to the locked configuration such that the anchor member 102 abuts a distal surface of the far bone (bone B). The flexible member 104 may then be tensioned and loosely tied to the flexible member 104' of a similarly inserted second bone anchor 101' such that the tension of the flexible members 104, 104' is maintained, fixing the bones A, B relative to one another. It should be noted that the flexible members 104, 104' should be loosely tied such that the flexible members 104, 104' do not become load bearing strands. When a load weight on either of the flexible members 104, 104' is too great, the flexible members 104, 104' may break, preventing removal of the anchor 102.

Figure 4:
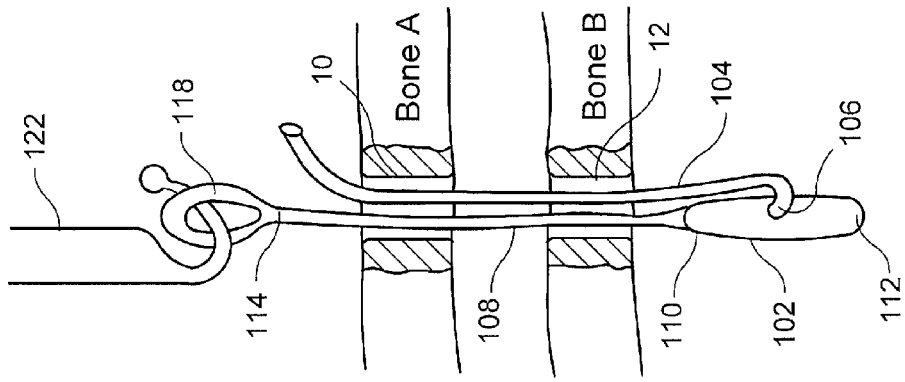
FIG. 4 shows a side view of the first anchor device of FIG. 3, in a removal configuration.
Figure 3:
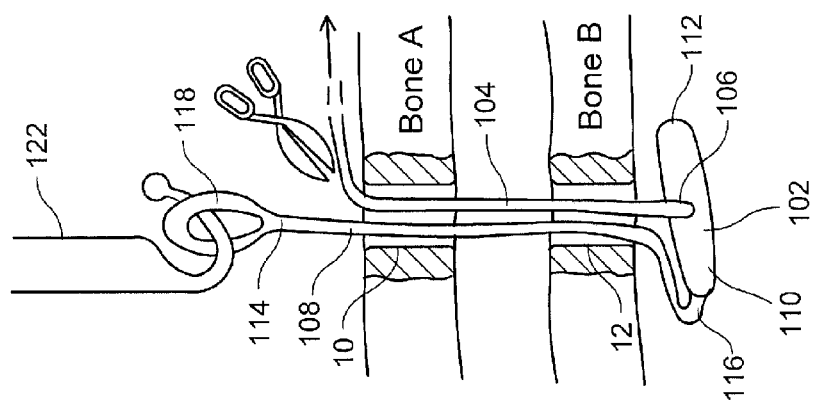
FIG. 3 shows a side view of the first anchor device of FIG. 2, with a hook inserted through a portion of a removal element thereof.
Figure 6:
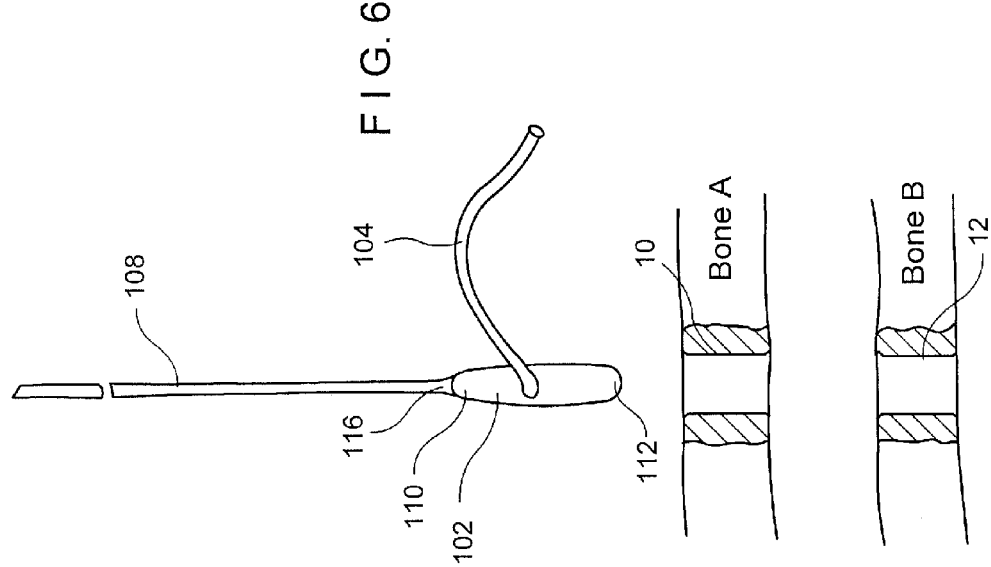
FIG. 6 shows a side view of the first anchor device of FIG. 5 being removed from a body.
Figure 5:
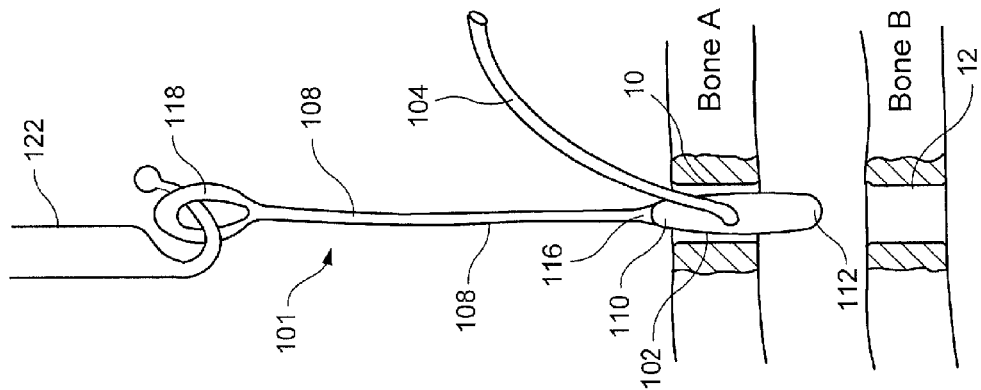
FIG. 5 shows a side view of the first anchor device of FIG. 4 being removed from a bone.

As shown in FIG. 3, to remove the bone anchor 101 after it has been implanted, an instrument 122 may be hooked into the loop 118 at the proximal end of the removal element 108 to hold the removal element 108 as the flexible member 104 is severed. Cutting the flexible member 104 releases the tension along the flexible member 104, permitting the anchor member 102 to be moved to the removal configuration, as shown in FIG. 4. The removal element 108 is tensioned drawing the first end 110 of the anchor member 102 toward the hole 12 until the first end 110 of the anchor member 102 enters the hole 12. Contact with the hole 12 then aligns the anchor member 102 with an axis of the holes 10, 12 facilitating removal of the anchor member 102 from the bones A, B. Thus, as shown in FIG. 5, the removal element 108 may be drawn proximally via the hook instrument 122 to remove the bone anchor 101 from the holes 10, 12 of the bones A, B, through which the bone anchor 101 was initially inserted. As shown in FIG. 6, the anchor member 102 and a remaining length of the flexible member 104 attached thereto are entirely removed from the bones A, B. It will be understood by those of skill in the art that where the system 100 includes more than one bone anchor, the second bone anchor 101' may be similarly removed.

Figure 7:
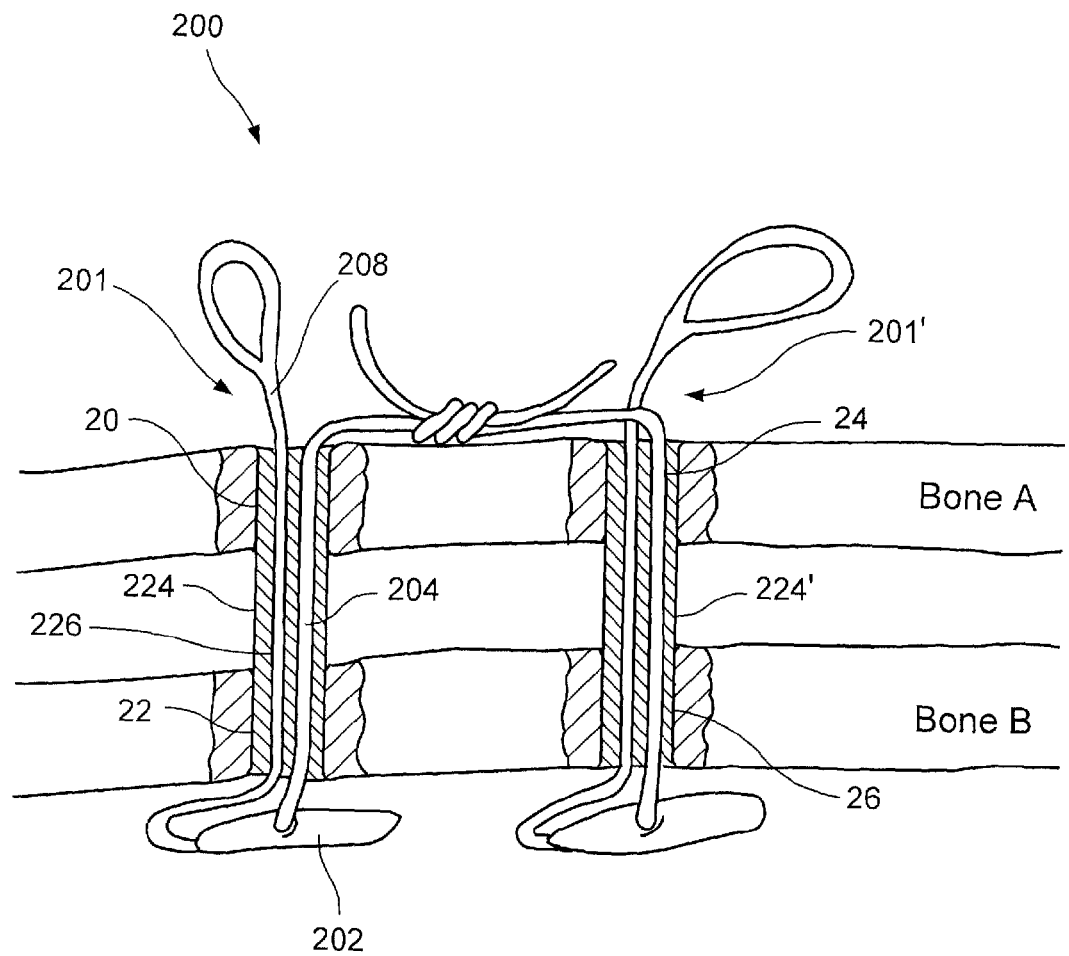
FIG. 7 shows a side view of a system according to a further exemplary embodiment of the present invention.

As shown in FIG. 7, a system 200 according to a further embodiment of the present invention comprises a bone anchor 201 and further comprises an insert 224 sized and shaped to be inserted into holes 20, 22 drilled through bones A, B, respectively, in alignment with one another, to prevent bone ingrowth therein and to facilitate removal of the bone anchor 201 therefrom. The bone anchor 201 is substantially similar to the bone anchor 101 comprising an anchor member 202 attached to a distal end 206 of a flexible member 204 and movable between an insertion configuration and a locked configuration. The bone anchor 201 also similarly comprises a removal element 208 attached to a first end 214 or the anchor member 202 via which the bone anchor 201 may be removed from bones A, B after insertion thereof. Prior to insertion of the bone anchor 201 through the holes 10, 12, however, the insert 224 may be inserted through the holes 20, 22 to prevent bone ingrowth around a subsequently inserted bone anchor 201.

The insert 224 may be substantially tubular including a lumen 226 extending therethrough sized to permit the bone anchor 201 to be inserted therethrough, substantially as described above in regard to the system 100. The insert 224 may be formed of a material such as, for example, PCU or silicone, which ensures that no loads are transferred and motion is preserved between the bones A, B. Similarly to the system 100, the system 200 may include a second bone anchor 201' which is also substantially similar to the bone anchor 101, which may be inserted through a second set of corresponding holes 24, 26 of the bones A, B. Where it is desired to utilize the second bone anchor 201', the system 200 may also comprise a second insert 224' inserted through the holes 24, 26 prior to insertion of the second bone anchor 201'. It will be understood by those of skill in the art that the bone anchor 201 may be inserted and removed substantially similarly to the bone anchor 101, as described above in regard to the system 100.

Figure 8:
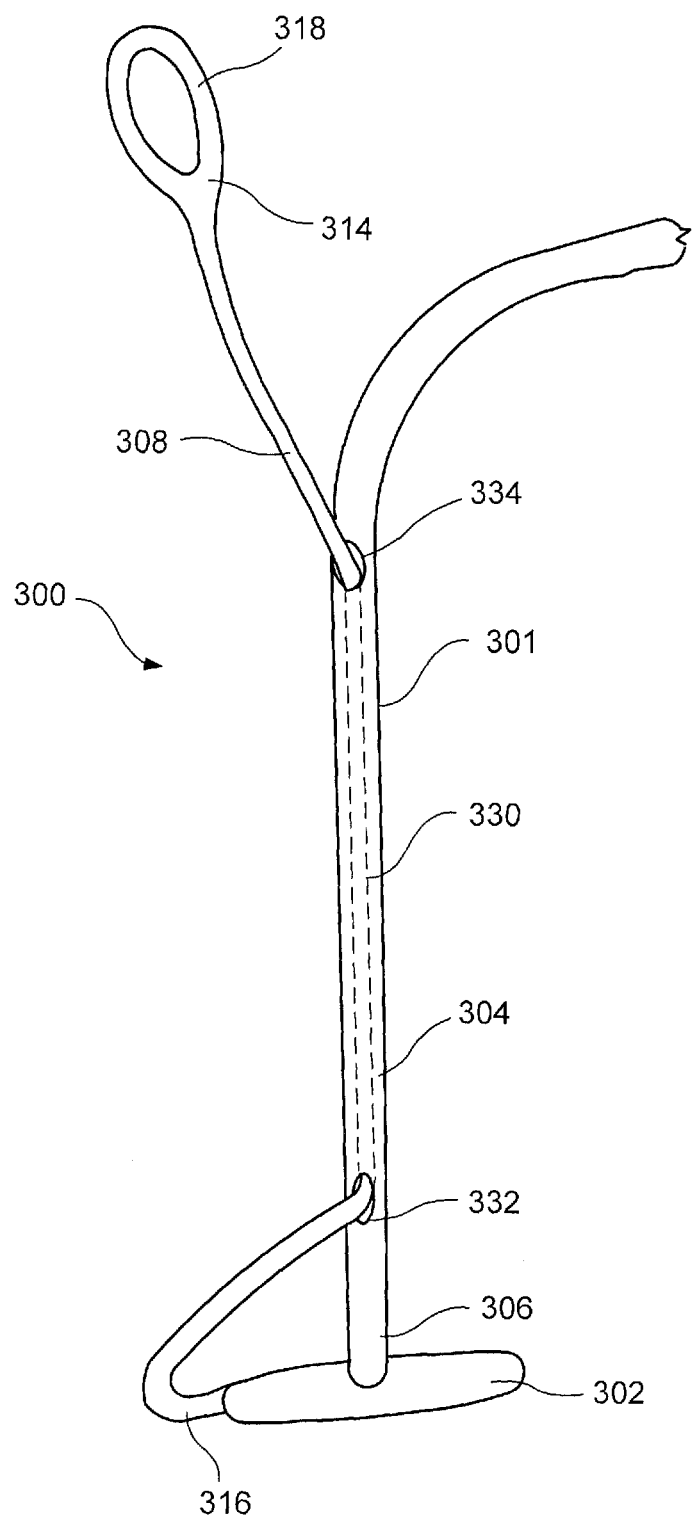
FIG. 8 shows a side view of a flexible member of a first anchor device of a system of another exemplary embodiment of the present invention

As shown in FIG. 8, a system 300 according to an exemplary embodiment of the present invention comprises a bone anchor 301, which may be substantially similar to the bone anchors 101, 201, described above. Similarly to the bone anchors 101, 201, the bone anchor 301 includes an anchor member 302 attached to a distal end 306 of a flexible member 304 and a removal element 308. A portion of the flexible member 304, however, is hollow and includes a channel 330 extending therein. The channel 330 has an inlet 332 and an outlet 334 located on a sidewall of the flexible member 304. The removal element 308 is arranged so that it is threaded from a distal end 316 attached to the anchor member 302 through the inlet 332 and out of the outlet 334 to a proximal end 314. The proximal end 314 may include a loop 318 or other grippable member suitable for facilitating removal of the anchor member 302 from a bone or bones. The insertion and removal process is as described for the systems 100 and 200, with the exception that the pulling of the loop 318 causes the removal element 308 to be drawn proximally in through the inlet 332 and out through the outlet 334 to orient the anchor member 302 for ease of insertion and removal.

It will be apparent to those skilled in the art that element of the systems 100, 200 and 300 can be incorporated and used interchangeably. For example, FIG. 7 shows a system where two inserts 224 are used, but it is of course possible that only one insert could be used. It is also of course possible that for one of the bone anchors 101, 101', 200 and 201', the bone anchor 300 could be used. It will be understood by those of skill in the art that other interchanging of elements are also possible.

It will be apparent to those skilled in the art that various modifications and variations can be made in the structure and methodology of the present invention, without departing from the spirit or scope of the invention. Thus, it is intended that the present invention cover the modifications and variations of this invention provided that they come within the scope of the appended claims and their equivalents.

What is claimed is:

1. An anchoring device, comprising:
   a flexible member extending from a proximal end to a distal end;
   an elongated anchor member extending from a first end to a second end and attached to the distal end of the flexible member such that the anchor member is movable between an insertion configuration in which the anchor member is substantially parallel to the flexible member and a locked configuration in which the anchor member is substantially perpendicular to the flexible member; and
   a flexible removal element extending from a proximal end to a distal end attached to the first end of the anchor member, a length of the removal element being selected so that, when the anchor member is implanted in a desired location, the removal element extends back along an insertion path through which the anchor member was inserted to the desired location so that drawing the removal element proximally out of the path moves the anchor member to the insertion configuration and draws the anchor member through the insertion path.

2. The device of claim 1, wherein the proximal end of the removal element includes a loop.

3. The device of claim 1, wherein the removal element is colored such that it is easily visible and differentiated from the flexible member.

4. The device of claim 1, wherein the flexible member is one of a suture, thread, cable and wire.

5. The device of claim 1, wherein the removal element is one of a suture, thread, cable and wire.

6. The device of claim 1, wherein the distal end of the flexible member is attached to a portion of the anchor member approximately midway between the first end and the second end.

7. The device of claim 1, wherein the flexible member includes a channel extending therethrough along a portion thereof from an inlet along a sidewall thereof to an outlet along a sidewall thereof, the removal element passed through the channel from the inlet to the outlet such that the proximal end of the removal element extends proximally out of the outlet.

* * * * *